(12) United States Patent
Uensal et al.

(10) Patent No.: US 8,822,091 B2
(45) Date of Patent: *Sep. 2, 2014

(54) PROTON-CONDUCTING MEMBRANE AND USE THEREOF

(75) Inventors: Oemer Uensal, Mainz (DE); Gunter Christ, Wallrabenstein (DE); Kathrin Wirth, Baselich (DE)

(73) Assignee: BASF Fuel Cell GmbH (DE)

( * ) Notice: Subject to any disclaimer, the term of this patent is extended or adjusted under 35 U.S.C. 154(b) by 1709 days.

This patent is subject to a terminal disclaimer.

(21) Appl. No.: 10/584,965

(22) PCT Filed: Dec. 30, 2004

(86) PCT No.: PCT/EP2004/014829
§ 371 (c)(1),
(2), (4) Date: Nov. 7, 2008

(87) PCT Pub. No.: WO2005/063862
PCT Pub. Date: Jul. 14, 2005

(65) Prior Publication Data
US 2009/0214920 A1 Aug. 27, 2009

(30) Foreign Application Priority Data
Dec. 30, 2003 (DE) .................................. 103 61 932

(51) Int. Cl.
| | |
|---|---|
| *H01M 8/04* | (2006.01) |
| *H01M 8/00* | (2006.01) |
| *H01M 8/10* | (2006.01) |
| *C08G 73/18* | (2006.01) |
| *C07F 9/09* | (2006.01) |
| *C08J 5/20* | (2006.01) |
| *H01M 8/02* | (2006.01) |
| *H01M 8/24* | (2006.01) |
| *H01M 8/12* | (2006.01) |

(52) U.S. Cl.
CPC ........ *H01M 8/04089* (2013.01); *H01M 8/0247* (2013.01); *H01M 8/04007* (2013.01); *H01M 8/2425* (2013.01); *H01M 8/1213* (2013.01); *Y02E 60/521* (2013.01); *C07F 9/091* (2013.01); *C08G 73/18* (2013.01)
USPC ........... 429/433; 429/400; 429/479; 429/491; 528/423; 521/27; 558/177

(58) Field of Classification Search
CPC .......... H01M 8/04089; H01M 8/0247; H01M 8/04007; H01M 8/2425; H01M 8/1213; Y02E 60/521; C07F 9/091; C08G 73/18
USPC .............. 429/33, 433, 400, 479, 491; 521/27; 528/423; 558/177
See application file for complete search history.

(56) References Cited

U.S. PATENT DOCUMENTS

| | | | |
|---|---|---|---|
| 3,600,435 A * | 8/1971 | Rendal et al. .................... 562/20 |
| 4,622,276 A | 11/1986 | Walsh | |
| 5,599,639 A | 2/1997 | Sansone et al. | |
| 7,235,320 B2 | 6/2007 | Calundann et al. | |
| 7,384,552 B2 | 6/2008 | Calundann et al. | |
| 7,540,984 B2 | 6/2009 | Calundann et al. | |
| 7,883,818 B2 | 2/2011 | Kiefer et al. | |
| 2002/0161220 A1* | 10/2002 | Pankiewicz et al. ......... 536/26.2 |
| 2004/0096734 A1 | 5/2004 | Calundann et al. | |
| 2004/0127588 A1 | 7/2004 | Calumdann et al. | |
| 2004/0127687 A1* | 7/2004 | Casida et al. ................. 530/350 |
| 2005/0053820 A1 | 3/2005 | Calundann et al. | |
| 2005/0084727 A1 | 4/2005 | Kiefer et al. | |
| 2005/0118477 A1* | 6/2005 | Kiefer et al. .................... 429/33 |
| 2005/0147859 A1 | 7/2005 | Kiefer et al. | |
| 2005/0175879 A1 | 8/2005 | Kiefer et al. | |
| 2005/0181254 A1 | 8/2005 | Uensal et al. | |
| 2005/0244694 A1 | 11/2005 | Kiefer et al. | |
| 2006/0008690 A1 | 1/2006 | Uensal et al. | |
| 2006/0127705 A1 | 6/2006 | Kiefer et al. | |
| 2007/0055045 A1 | 3/2007 | Kiefer et al. | |
| 2008/0038624 A1 | 2/2008 | Belack et al. | |
| 2008/0050514 A1 | 2/2008 | Calundann et al. | |
| 2009/0214920 A1 | 8/2009 | Uensal et al. | |
| 2009/0214921 A1 | 8/2009 | Uensal et al. | |
| 2010/0181697 A1 | 7/2010 | Uensal et al. | |
| 2010/0227252 A1 | 9/2010 | Kiefer et al. | |
| 2011/0065020 A1 | 3/2011 | Uensal et al. | |
| 2011/0318671 A1 | 12/2011 | Uensal et al. | |

FOREIGN PATENT DOCUMENTS

| | | | | |
|---|---|---|---|---|
| DE | 10117686 A1 | 10/2002 | | |
| DE | 10117687 | * 10/2002 | ................. C08J 5/22 |
| DE | 10117687 A1 | 10/2002 | | |
| EP | 1 202 365 | 5/2002 | | |
| GB | 737036 | * 9/1955 | | |
| GB | 737036 A | 9/1955 | | |
| WO | WO-02/081547 | 10/2002 | | |
| WO | WO-02/088219 | 11/2002 | | |
| WO | WO-03/022412 | 3/2003 | | |

(Continued)

OTHER PUBLICATIONS

K. Kanamura et al., "Perfluoro-ethylene-1,2-bis-phosphonic Acid Fuel Cell Elctrolyte", J. Electrochem. Soc., vol. 143, No. 9, pp. 2765-2770, Sep. 1996.
U.S. Appl. No. 10/585,057, Uensal et al.

*Primary Examiner* — Patrick Ryan
*Assistant Examiner* — Aaron Greso
(74) *Attorney, Agent, or Firm* — Drinker Biddle & Reath LLP

(57) ABSTRACT

The present invention relates to a novel proton-conducting polymer membrane based on polyazoles which can, owing to its excellent chemical and thermal properties, be used for a variety of purposes and is particularly suitable as a polymer-electrolyte membrane (PEM) for the production of membrane electrode units for so-called PEM fuel cells.

35 Claims, No Drawings

(56) References Cited

FOREIGN PATENT DOCUMENTS

| WO | WO-03/074596 | | 9/2003 | |
| --- | --- | --- | --- | --- |
| WO | WO 03/074597 | * | 9/2003 | ............... C08J 7/16 |
| WO | WO-03/074597 | | 9/2003 | |
| WO | WO-03/075389 | | 9/2003 | |
| WO | WO-03/092090 | | 11/2003 | |
| WO | WO-03/096464 | | 11/2003 | |
| WO | WO-2005/063851 | | 7/2005 | |
| WO | WO-2005/063851 A1 | | 7/2005 | |
| WO | WO-2005/063852 | | 7/2005 | |
| WO | WO-2005/063852 A1 | | 7/2005 | |
| WO | WO-2005/063862 | | 7/2005 | |

* cited by examiner

PROTON-CONDUCTING MEMBRANE AND USE THEREOF

RELATED APPLICATIONS

This application is a national stage application (under 35 U.S.C. §371) of PCT/EP2004/014829, filed Dec. 30, 2004, which claims benefit of Germany application 10361932.1, filed Dec. 30, 2003.

The present invention relates to a novel proton-conducting polymer membrane based on polyazoles which can, owing to its excellent chemical and thermal properties, be used for a variety of purposes and is particularly suitable as a polymer-electrolyte membrane (PEM) in so-called PEM fuel cells.

Polyazoles such as polybenzimidazoles (®Celazole) have been known for a long time. The production of such polybenzimidazoles (PBI) is usually conducted by reacting 3,3',4,4'-tetraaminobiphenyl with isophthalic acid or its esters in the melt. The resulting prepolymer solidifies in the reactor und is subsequently comminuted mechanically. The pulverulent prepolymer is then fully polymerised in a solid-state polymerisation at temperatures of up to 400° C. and the desired polybenzimidazole is obtained.

To produce polymer films, the PBI is dissolved in an additional step in polar, aprotic solvents such as dimethylacetamide (DMAc) and a film is produced by means of classical processes.

Proton-conducting, i.e. acid-doped polyazole membranes for use in PEM fuel cells are already known. The alkaline polyazole films are doped with concentrated phosphoric acid or sulphuric acid and then act as proton conductors and separators in so-called polymer electrolyte membrane fuel cells (PEM fuel cells).

Due to the excellent properties of the polyazole polymer, such polymer electrolyte membranes—processed to produce membrane electrode units (MEUs)—can be employed in fuel cells at long-term operating temperatures above 100° C., in particular above 120° C. This high long-term operating temperature allows increasing the activity of the catalysts based on noble metals which are included in the membrane electrode unit (MEU). Especially when the so-called reformates from hydrocarbons are used, the reformer gas contains considerable amounts of carbon monoxide which usually have to be removed by means of an elaborate gas conditioning or gas purification process. Owing to the possibility to increase the operating temperature, significantly higher concentrations of CO impurities can be tolerated permanently.

By employing polymer electrolyte membranes based on polyazole polymers, it is possible, on the one hand, to partly dispense with the elaborate gas conditioning or gas purification process and, on the other hand, to reduce the catalyst load in the membrane electrode unit. These are both indispensable preconditions for a large-scale use of PEM fuel cells as otherwise the cost for a PEM fuel cell system is too high.

The previously known acid-doped polymer membranes based on polyazoles already display a beneficial property profile. However, due to the intended applications for PEM fuel cells, in particular in the automobile sector and the decentralised electricity and heat generation (stationary sector), these need to be improved altogether. Furthermore, the previously known polymer membranes have a high content of dimethylacetamide (DMAc) which cannot be removed completely by means of known drying methods. The German patent application No. 10109829.4 describes a polymer membrane based on polyazoles in which the DMAc contamination was removed.

Polymer membranes based on polyazoles which are produced from polyphosphoric acids are known from the German patent applications No. 10117686.4, 10117687.2 and 10144815.5. These membranes display an excellent performance, in particular at operating temperatures above 100° C. However, these membranes have the disadvantage that they exhibit a relatively high overvoltage, in particular at the cathode.

It is an object of the present invention to provide polymer membranes that are based on polyazoles and contain organic acid, which, on the one hand, display the advantages of the polymer membrane based on polyazoles in terms of application technology and, on the other hand, have an increased specific conductivity, in particular at operating temperatures above 100° C., and additionally exhibit a markedly lower overvoltage, in particular at the cathode.

We have now found that a proton-conducting membrane based on polyazoles can be obtained when the underlying polyazole prepolymers are suspended or dissolved in organic phosphonic anhydrides, brought into a thin form by means of a doctor blade and fully polymerised in the organic phosphonic anhydrides.

The object of the present invention is a proton-conducting polymer membrane based on polyazoles which can be obtained by a process comprising the steps of
A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C., preferably up to 300° C.,
B) dissolving the solid prepolymer obtained in accordance with step A) in organic phosphonic anhydrides with formation of a solution and/or dispersion,
C) heating the solution obtainable in accordance with step B) under inert gas to temperatures of up to 300° C., preferably up to 280° C., with formation of the dissolved polyazole polymer,
D) forming a membrane using the solution of the polyazole polymer in accordance with step C) on a support and
E) treatment of the membrane formed in step D) until it is self-supporting.

The aromatic and heteroaromatic tetramino compounds used according to the invention are preferably 3,3',4,4'-tetraminobiphenyl, 2,3,5,6-tetraminopyridine, 1,2,4,5-tetraminobenzene, 3,3',4,4'-tetraminodiphenyl sulphone, 3,3',4,4'-tetraminodiphenyl ether, 3,3',4,4'-tetraminobenzophenone, 3,3',4,4'-tetraminodiphenylmethane and 3,3',4,4'-tetraminodiphenyldimethylmethane and their salts, in particular their monohydrochloride, dihydrochloride, trihydrochloride and tetrahydrochloride derivatives.

The aromatic carboxylic acids used according to the invention are dicarboxylic and tricarboxylic acids and tetracarboxylic acids or their esters or their anhydrides or their acid chlorides. The term aromatic carboxylic acids likewise also comprises heteroaromatic carboxylic acids. Preferably, the aromatic dicarboxylic acids are isophthalic acid, terephthalic acid, phthalic acid, 5-hydroxyisophthalic acid, 4-hydroxyisophthalic acid, 2-hydroxyterephthalic acid, 5-aminoisophthalic acid, 5-N,N-dimethylaminoisophthalic acid, 5-N,N-diethylaminoisophthalic acid, 2,5-dihydroxyterephthalic acid, 2,6-dihydroxyisophthalic acid, 4,6-dihydroxyisophthalic acid, 2,3-dihydroxyphthalic acid, 2,4-dihydroxyphthalic acid, 3,4-dihydroxyphthalic acid, 3-fluorophthalic acid, 5-fluoroisophthalic acid, 2-fluoroterephthalic acid, tetrafluorophthalic acid, tetrafluoroisophthalic acid, tetrafluoroterephthalic acid, 1,4-naphthalenedicarboxylic acid, 1,5-naphthalenedicarboxylic acid, 2,6-naphthalenedicarboxylic acid, 2,7-naphthalenedicarboxylic acid, diphenic acid, 1,8-dihydroxynaphthatene-3,6-dicarboxylic acid, diphenyl ether-4,4'-dicarboxylic acid, benzophenone-4,4'-dicarboxylic acid, diphenylsulphone-4,4'-dicarboxylic acid, biphenyl-4,4'-dicarboxylic acid, 4-trifluoromethylphthalic acid, 2,2-bis(4-carboxyphenyl)hexafluoropropane, 4,4'-stilbenedicarboxylic acid, 4-carboxycinnamic acid or their C1-C20 alkyl esters or C5-C12 aryl esters or their acid anhydrides or their acid chlorides. The aromatic tricarboxylic acids, tetracarboxylic acids or their C1-C20 alkyl esters or C5-C12 aryl esters or their acid anhydrides or their acid chlorides are preferably 1,3,5-benzenetricarboxylic acid (trimesic acid), 1,2,4-benzenetricarboxylic acid (trimellitic acid), (2-Carboxyphenyl)iminodiessigsäure, 3,5,3'-Biphenyltricarbonsäure, 3,5,4'-Biphenyltricarbonsäure.

The aromatic tetracarboxylic acids or their C1-C20 alkyl esters or C5-C12 aryl esters or their acid anhydrides or their acid chlorides are preferably 3,5,3',5'-biphenyltetracarboxylic acid, 1,2,4,5-benzenetetracarboxylic acid, benzophenonetetracarboxylic acid, 3,3',4,4'-biphenyltetracarboxylic acid, 2,2',3,3'-biphenyltetracarboxylic acid, 1,2,5,6-naphthalenetetracarboxylic acid, 1,4,5,8-naphthalenetetracarboxylic acid.

The heteroaromatic carboxylic acids used according to the invention are heteroaromatic dicarboxylic and tricarboxylic acids and tetracarboxylic acids or their esters or their anhydrides. Heteroaromatic carboxylic acids are understood to mean aromatic systems which contain at least one nitrogen, oxygen, sulphur or phosphor atom in the aromatic group. Preferably, these are pyridine-2,5-dicarboxylic acid, pyridine-3,5-dicarboxylic acid, pyridine-2,6-dicarboxylic acid, pyridine-2,4-dicarboxylic acid, 4-phenyl-2,5-pyridinedicarboxylic acid, 3,5-pyrazoledicarboxylic acid, 2,6-pyrimidinedicarboxylic acid, 2,5-pyrazinedicarboxylic acid, 2,4,6-pyridinetricarboxylic acid, benzimidazole-5,6-dicarboxylic acid and their C1-C20 alkyl esters or C5-C12 aryl esters or their acid anhydrides or their acid chlorides.

The content of tricarboxylic acids or tetracarboxylic acids (based on dicarboxylic acid used) is between 0 and 30 mol-%, preferably 0.1 and 20 mol-%, in particular 0.5 and 10 mol-%.

The aromatic and heteroaromatic diaminocarboxylic acids used according to the invention are preferably diaminobenzoic acid and its monohydrochloride and dihydrochloride derivatives.

Preferably, mixtures of at least 2 different aromatic carboxylic acids are used in step A). Particularly preferably, mixtures are used which also contain heteroaromatic carboxylic acids additional to aromatic carboxylic acids. The mixing ratio of aromatic carboxylic acids to heteroaromatic carboxylic acids is from 1:99 to 99:1, preferably 1:50 to 50:1.

These mixtures are in particular mixtures of N-heteroaromatic dicarboxylic acids and aromatic dicarboxylic acids. Non-limiting examples of these are isophthalic acid, terephthalic acid, phthalic acid, 2,5-dihydroxyterephthalic acid, 2,6-dihydroxyisophthalic acid, 4,6-dihydroxyisophthalic acid, 2,3-dihydroxyphthalic acid, 2,4-dihydroxyphthalic acid, 3,4-dihydroxyphthalic acid, 1,4-naphthalenedicarboxylic acid, 1,5-naphthalenedicarboxylic acid, 2,6-naphthalenedicarboxylic acid, 2,7-naphthalenedicarboxylic acid, diphenic acid, 1,8-dihydroxynaphthalene-3,6-dicarboxylic acid, diphenyl ether-4,4'-dicarboxylic acid, benzophenone-4,4'-dicarboxylic acid, diphenylsulphone-4,4'-dicarboxylic acid, biphenyl-4,4'-dicarboxylic acid, 4-trifluoromethylphthalic acid, pyridine-2,5-dicarboxylic acid, pyridine-3,5-dicarboxylic acid, pyridine-2,6-dicarboxylic acid, pyridine-2,4-dicarboxylic acid, 4-phenyl-2,5-pyridinedicarboxylic acid, 3,5-pyrazoledicarboxylic acid, 2,6-pyrimidinedicarboxylic acid, 2,5-pyrazinedicarboxylic acid.

The prepolymerisation in accordance with step A) leads, with the chosen temperature range and using 3,3',4,4'-tetraminobiphenyl (TAB) and isophthalic esters (OR), to the formation of the corresponding amides or imines (cf. following scheme):

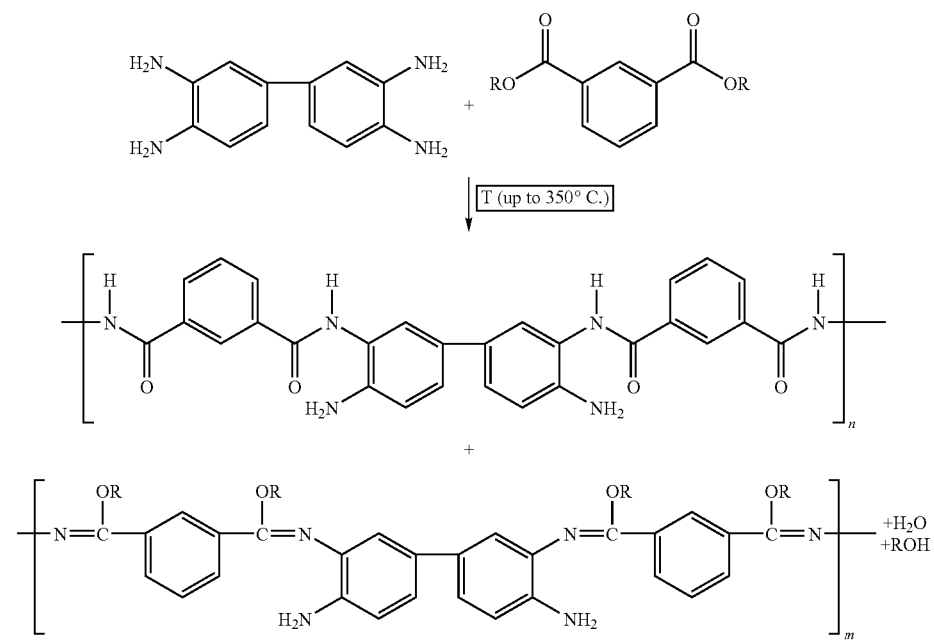

The obtained prepolymer solidifies in the reaction and can optionally, following coarse grinding, be dissolved or suspended in the organic phosphonic acid.

The organic phosphonic anhydrides used in step B) are cyclic compounds of the formula

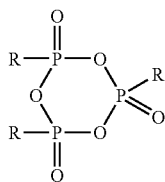

or linear compounds of the formula

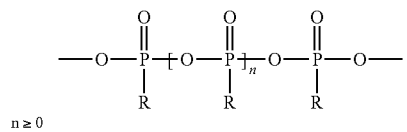

$n \geq 0$ or anhydrides of the multiple organic phosphonic acids, such as of the formula of anhydrides of the diphosphonic acid

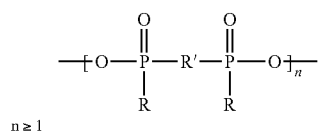

$n \geq 1$ wherein the radicals R and R' are identical or different and represent a $C_1$-$C_{20}$ carbon-containing group.

Within the scope of the present invention, a $C_1$-$C_{20}$ carbon-containing group is understood to mean preferably the radicals $C_1$-$C_{20}$ alkyl, particularly preferably methyl, ethyl, n-propyl, i-propyl, n-butyl, i-butyl, s-butyl, t-butyl, n-pentyl, s-pentyl, cyclopentyl, n-hexyl, cyclohexyl, n-octyl or cyclooctyl, $C_1$-$C_{20}$ alkenyl, particularly preferably ethenyl, propenyl, butenyl, pentenyl, cyclopentenyl, hexenyl, cyclohexenyl, octenyl or cyclooctenyl, $C_1$-$C_{20}$ alkynyl, particular preferably ethynyl, propynyl, butynyl, pentynyl, hexynyl or octynyl, $C_6$-$C_{20}$ aryl, particularly preferably phenyl, biphenyl, naphthyl or anthracenyl, $C_1$-$C_{20}$ fluoroalkyl, particularly preferably trifluoromethyl, pentafluoroethyl or 2,2,2-trifluoroethyl, $C_6$-$C_{20}$ aryl, particularly preferably phenyl, biphenyl, naphthyl, anthracenyl, triphenylenyl, [1,1';3',1'']-terphenyl-2'-yl, binaphthyl or phenanthrenyl, $C_6$-$C_{20}$ fluoroaryl, particularly preferably tetrafluorophenyl or heptafluoronaphthyl, $C_6$-$C_{20}$ alkoxy, particularly preferably methoxy, ethoxy, n-propoxy, i-propoxy, n-butoxy, i-butoxy, s-butoxy or t-butoxy, $C_6$-$C_{20}$ aryloxy, particularly preferably phenoxy, naphthoxy, biphenyloxy, anthracenyloxy, phenanthrenyloxy, $C_7$-$C_{20}$ arylalkyl, particularly preferably phenoxy, naphthoxy, biphenyloxy, anthracenyloxy, phenanthrenyloxy, $C_7$-$C_{20}$ arylalkyl, particularly preferably o-tolyl, m-tolyl, p-tolyl, 2,6-dimethylphenyl, 2,6-diethylphenyl, 2,6-di-1-propylphenyl, 2,6-di-t-butylphenyl, o-t-butylphenyl, m-t-butylphenyl, p-t-butylphenyl, $C_7$-$C_{20}$ alkylaryl, particularly preferably benzyl, ethylphenyl, propylphenyl, diphenylmethyl, triphenylmethyl or naphthalenylmethyl, $C_7$-$C_{20}$ aryloxyalkyl, particularly preferably o-methoxyphenyl, m-phenoxymethyl, p-phenoxymethyl, $C_{12}$-$C_{20}$ aryloxyaryl, particularly preferably p-phenoxyphenyl, $C_5$-$C_{20}$ heteroaryl, particularly preferably 2-pyridyl, 3-pyridyl, 4-pyridyl, quinolinyl, isoquinolinyl, acridinyl, benzoquinolinyl or benzoisoquinolinyl, $C_4$-$C_{20}$ heterocycloalkyl, particularly preferably furyl, benzofuryl, 2-pyrrolidinyl, 2-indolyl, 3-indolyl, 2,3-dihydroindolyl, $C_8$-$C_{20}$ arylalkenyl, particularly preferably o-vinylphenyl, m-vinylphenyl, p-vinylphenyl, $C_8$-$C_{20}$ arylalkynyl, particularly preferably o-ethynylphenyl, m-ethynylphenyl or p-ethynylphenyl, $C_2$-$C_{20}$ heteroatom-containing group, particularly preferably carbonyl, benzoyl, oxybenzoyl, benzoyloxy, acetyl, acetoxy or nitril, where one or more $C_1$-$C_{20}$ carbon-containing groups can form a cyclic system.

In the above-mentioned $C_1$-$C_{20}$ carbon-containing groups, one or more $CH_2$ groups that are not adjacent to each other can be replaced by —O—, —S—, —$NR^1$— or —$CONR^2$— and one or more H atoms can be replaced by F.

In the above-mentioned $C_1$-$C_{20}$ carbon-containing groups which can include the aromatic systems, one or more CH groups that are not adjacent to each other can be replaced by —O—, —S—, —$NR^1$— or —$CONR^2$— and one or more H atoms can be replaced by F.

The radicals $R^1$ and $R^2$ are identical or different at each occurrence of H or are an aliphatic or aromatic hydrocarbon radical having 1 to 20 C atoms.

Particularly preferred are organic phosphonic anhydrides which are partially fluorinated or perfluorinated.

The organic phosphonic anhydrides used in step B) are commercially available, for example the product ®T3P (propane phosphonic anhydride) from the company Clariant.

The organic phosphonic anhydrides used in step B) can also be employed in combination with polyphosphoric acid and/or $P_2O_5$. The polyphosphoric acids are customary polyphosphoric acids as they are available, for example, from Riedel-de Haen. The polyphosphoric acids $H_{n+2}P_nO_{3n+1}$ (n>1) usually have a concentration of at least 83%, calculated as $P_2O_5$ (by acidimetry). Instead of a solution of the monomers, a dispersion/suspension can also be produced.

The organic phosphonic anhydrides used in step B) can also be employed in combination with single or multiple organic phosphonic acids.

The single and/or multiple organic phosphonic acids are compounds of the formula

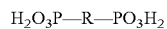

$n > 2$ wherein the radicals R are identical or different and represent a $C_{1-20}$ carbon-containing group.

Within the scope of the present invention, a $C_1$-$C_{20}$ carbon-containing group is understood to mean preferably the radicals $C_1$-$C_{20}$ alkyl, particularly preferably methyl, ethyl, n-propyl, i-propyl, n-butyl, i-butyl, s-butyl, t-butyl, n-pentyl, s-pentyl, cyclopentyl, n-hexyl, cyclohexyl, n-octyl or cyclooctyl, $C_6$-$C_{20}$ aryl, particularly preferably phenyl, biphenyl, naphthyl or anthracenyl, $C_1$-$C_{20}$ fluoroalkyl, particularly preferably trifluoromethyl, pentafluoroethyl or 2,2,2-trifluoroethyl, $C_6$-$C_{20}$ aryl, particularly preferably phenyl, biphenyl, naphthyl, anthracenyl, triphenylenyl, [1,1'3',1'']-terphenyl-2'-yl, binaphthyl or phenanthrenyl, $C_6$-$C_{20}$ fluoroaryl, particularly preferably tetrafluorophenyl or heptafluoronaphthyl, $C_1$-$C_{20}$ alkoxy, particularly preferably methoxy, ethoxy, n-propoxy, i-propoxy, n-butoxy, i-butoxy, s-butoxy or t-butoxy, $C_6$-$C_{20}$ aryloxy, particularly preferably phenoxy, naphthoxy, biphenyloxy, anthracenyloxy, phenanthrenyloxy, $C_7$-$C_{20}$ arylalkyl, particularly preferably o-tolyl, m-tolyl, p-tolyl, 2,6-dimethylphenyl, 2,6-diethylphenyl, 2,6-di-1-propylphenyl, 2,6-di-t-butylphenyl, o-t-butylphenyl, m-t-butylphenyl, p-t-butylphenyl, $C_7$-$C_{20}$ alkylaryl, particularly preferably benzyl, ethylphenyl, propylphenyl, diphenylmethyl, triphenylmethyl or naphthalenylmethyl, $C_7$-$C_{20}$ aryloxyalkyl, particularly preferably o-methoxyphenyl, m-phenoxymethyl, p-phenoxymethyl, $C_{12}$-$C_{20}$ aryloxyaryl, particularly preferably p-phenoxyphenyl, $C_5$-$C_{20}$ heteroaryl, particularly preferably 2-pyridyl, 3-pyridyl, 4-pyridyl, quinolinyl, isoquinolinyl, acridinyl, benzoquinolinyl or benzoisoquinolinyl, $C_4$-$C_{20}$ heterocycloalkyl, particularly preferably furyl, benzofuryl, 2-pyrrolidinyl, 2-indolyl, 3-indolyl, 2,3-dihydroindolyl, $C_2$-$C_{20}$ heteroatom-containing group, particularly preferably carbonyl, benzoyl, oxybenzoyl, benzoyloxy, acetyl, acetoxy or nitril, where one or more $C_1$-$C_{20}$ carbon-containing groups can form a cyclic system.

In the above-mentioned $C_1$-$C_{20}$ carbon-containing groups, one or more $CH_2$ groups that are not adjacent to each other can be replaced by —O—, —S—, —NR$^1$— or —CONR$^2$— and one or more H atoms can be replaced by F.

In the above-mentioned $C_1$-$C_{20}$ carbon-containing groups which can include the aromatic systems, one or more CH groups that are not adjacent to each other can be replaced by —O—, —S—, —NR$^1$— or —CONR$^2$— and one or more H atoms can be replaced by F.

The radicals R$^1$ and R$^2$ are identical or different at each occurrence of H or are an aliphatic or aromatic hydrocarbon radical having 1 to 20 C atoms.

Particularly preferred are organic phosphonic acids which are partially fluorinated or perfluorinated.

The organic phosphonic acids used in step B) are commercially available, for example the products from the company Clariant or Aldrich.

The organic phosphonic acids used in step B) comprise no vinyl-containing phosphonic acids as are described in the German patent application No. 10213540.1.

The mixture produced in step B) has a weight ratio of organic phosphonic anhydrides to the sum of all monomers of from 1:10,000 to 10,000:1, preferably 1:1000 to 1000:1, in particular 1:100 to 100:1. If these phosphonic anhydrides are used in a mixture with polyphosphoric acid or single and/or multiple organic phosphonic acids, these have to be considered in the phosphonic anhydrides.

In addition, further organophosphonic acids, preferably perfluorinated organic phosphonic acids can be added to the mixture produced in step B). This addition can be performed before, during or after the steps B) and C) as well as before step D). Through this, it is possible to control the viscosity.

The layer formation in accordance with step D is performed by means of measures known per se (pouring, spraying, application with a doctor blade) which are known from the prior art of polymer film production. Every support that is considered as inert under the conditions is suitable as a support. To adjust the viscosity, phosphoric acid (conc. phosphoric acid, 85%) can be added to the solution, where required. Through this, the viscosity can be adjusted to the desired value and the formation of the membrane be facilitated.

The layer produced in accordance with step D) has a thickness of from 20 to 4000 μm, preferably of from 30 to 3500 μm, in particular of from 50 to 3000 μm.

The polymer based on polyazole formed in step C) contains recurring azole units of the general formula (I) and/or (II) and/or (III) and/or (IV) and/or (V) and/or (VI) and/or (VII) and/or (VIII) and/or (IX) and/or (X) and/or (XI) and/or (XII) and/or (XIII) and/or (XIV) and/or (XV) and/or (XVI) and/or (XVII) and/or (XVIII) and/or (XIX) and/or (XX) and/or (XXI) and/or (XXII):

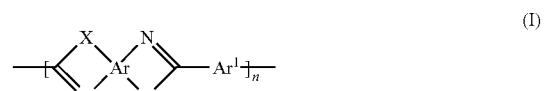

(I)

(II)

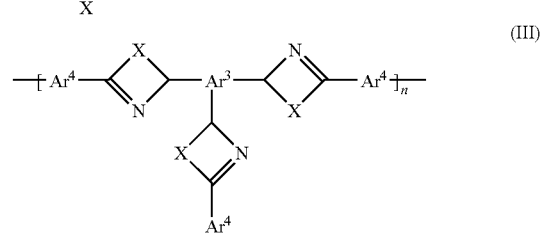

(III)

(IV)

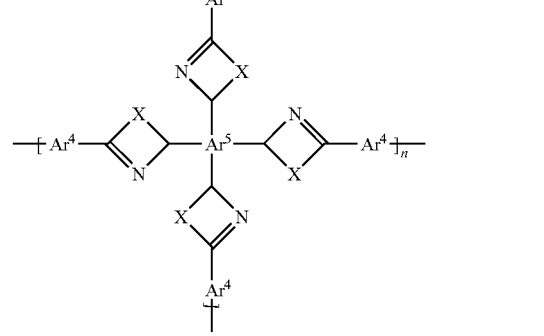

(V)

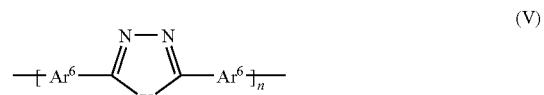

(VI)

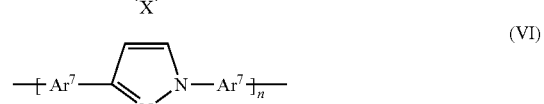

(VII)

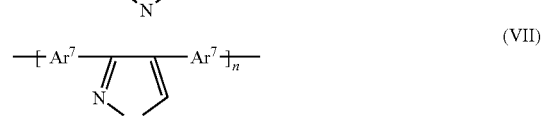

(VIII)

(IX)

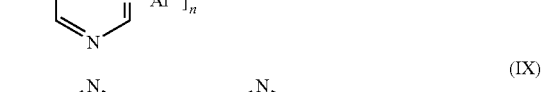

(X)

wherein

Ar are identical or different and represent a tetracovalent aromatic or heteroaromatic group which can be mononuclear or polynuclear, $Ar^1$ are identical or different and represent a bicovalent aromatic or heteroaromatic group which can be mononuclear or polynuclear, $Ar^2$ are identical or different and represent a bicovalent or tricovalent aromatic or heteroaromatic group which can be mononuclear or polynuclear, $Ar^3$ are identical or different and represent a tricovalent aromatic or heteroaromatic group which can be mononuclear or polynuclear, $Ar^4$ are identical or different and represent a tricovalent aromatic or heteroaromatic group which can be mononuclear or polynuclear, $Ar^5$ are identical or different and represent a tetracovalent aromatic or heteroaromatic group which can be mononuclear or polynuclear, $Ar^6$ are identical or different and represent a bicovalent aromatic or heteroaromatic group which can be mononuclear or polynuclear, $Ar^7$ are identical or different and represent a bicovalent aromatic or heteroaromatic group which can be mononuclear or polynuclear, $Ar^8$ are identical or different and represent a tricovalent aromatic or heteroaromatic group which can be mononuclear or polynuclear, $Ar^9$ are identical or different and represent a bicovalent or tricovalent or tetracovalent aromatic or heteroaromatic group which can be mononuclear or polynuclear, $Ar^{10}$ are identical or different and represent a bicovalent or tricovalent aromatic or heteroaromatic group which can be mononuclear or polynuclear, $Ar^{11}$ are identical or different and represent a bicovalent aromatic or heteroaromatic group which can be mononuclear or polynuclear, X are identical or different and represent oxygen, sulphur or an amino group which carries a hydrogen atom, a group having 1-20 carbon atoms, preferably a branched or unbranched alkyl or alkoxy group, or an aryl group as a further radical, R are identical or different and represent hydrogen, an alkyl group and an aromatic group, with the proviso that R in formula (XX) is not hydrogen, and n, m are each an integer greater than or equal to 10, preferably greater or equal to 100.

Preferred aromatic or heteroaromatic groups are derived from benzene, naphthalene, biphenyl, diphenyl ether, diphenylmethane, diphenyldimethylmethane, bisphenone, diphenylsulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzooxadiazole, benzopyridine, benzopyrazine, benzopyrazidine, benzopyrimidine, benzotriazine, indolizine, pyridopyridine, imidazopyrimidine, pyrazinopyrimidine, carbazole, aziridine, phenazine, benzoquinoline, phenoxazine, phenothiazine, acridizine, benzopteridine, phenanthroline and phenanthrene which optionally also can be substituted.

In this case, $Ar^1, Ar^4, Ar^6, Ar^7, Ar^8, Ar^9, Ar^{10}, Ar^{11}$ can have any substitution pattern, in the case of phenylene, for example, $Ar^1, Ar^4, Ar^6, Ar^7, Ar^8, Ar^9, Ar^{10}, Ar^{11}$ can be ortho-, meta- and para-phenylene. Particularly preferred groups are derived from benzene and biphenylene which optionally also can be substituted.

Preferred alkyl groups are short-chain alkyl groups having 1 to 4 carbon atoms, e.g. methyl, ethyl, n- or i-propyl and t-butyl groups.

Preferred aromatic groups are phenyl or naphthyl groups. The alkyl groups and the aromatic groups can be substituted.

Preferred substituents are halogen atoms, e.g. fluorine, amino groups, hydroxy groups or short-chain alkyl groups, e.g. methyl or ethyl groups.

Polyazoles having recurring units of the formula (I) are preferred where the radicals X within one recurring unit are identical.

The polyazoles can in principle also have different recurring units where their radicals X are different, for example. It is preferable, however, that a recurring unit has only identical radicals X.

Further preferred polyazole polymers are polyimidazoles, polybenzothiazoles, polybenzoxazoles, polyoxadiazoles, polyquinoxalines, polythiadiazoles, poly(pyridines), poly(pyrimidines) and poly(tetrazapyrenes).

In another embodiment of the present invention, the polymer containing recurring azole units is a copolymer or a blend which contains at least two units of the formulae (I) to (XXII) which differ from one another. The polymers can be in the form of block copolymers (diblock, triblock), segmented copolymers, random copolymers, periodic copolymers and/or alternating polymers.

In a particularly preferred embodiment of the present invention, the polymer containing recurring azole units is a polyazole which only contains units of the formulae (I) and/or (II).

The number of recurring azole units in the polymer is preferably an integer greater than or equal to 10. Particularly preferred polymers contain at least 100 recurring azole units.

Within the scope of the present invention, polymers containing recurring benzimidazole units are preferred. Some examples of the most appropriate polymers containing recurring benzimidazole units are represented by the following formulae:

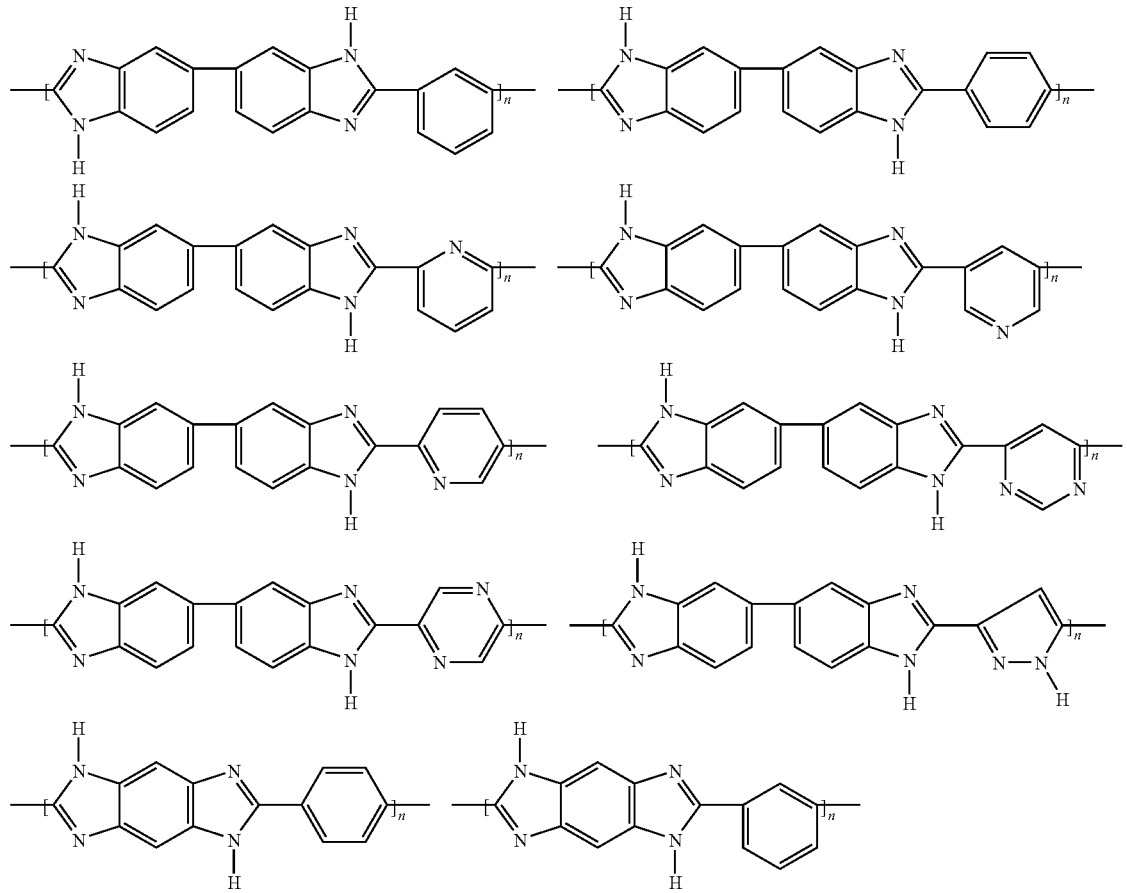

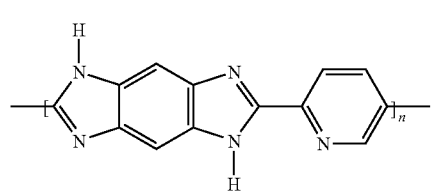
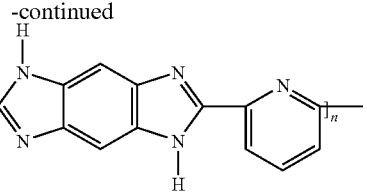

-continued

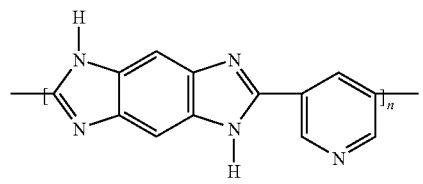
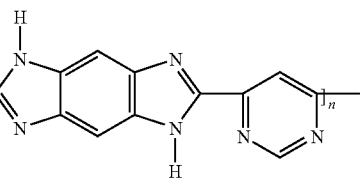

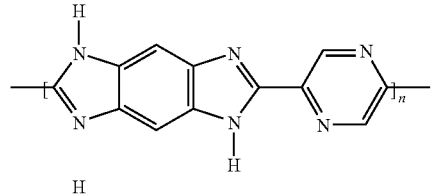
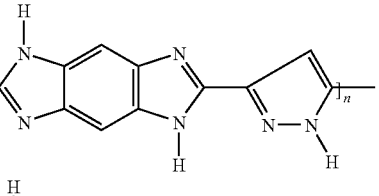

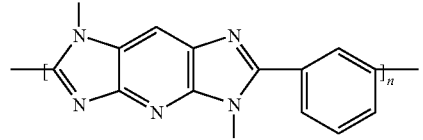
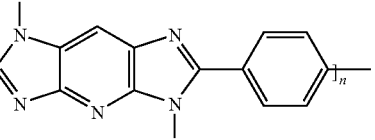

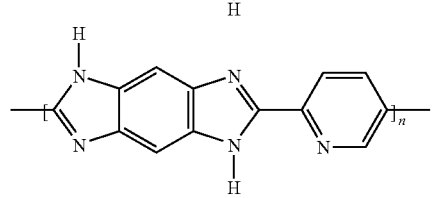
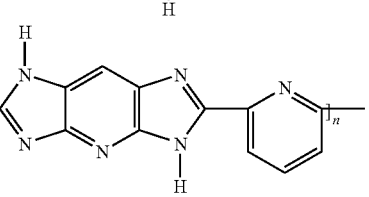

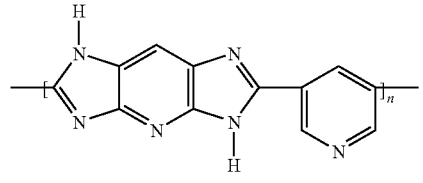
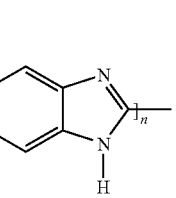

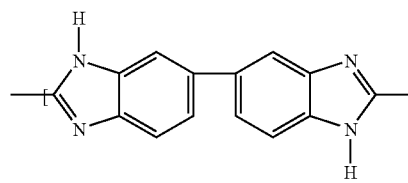
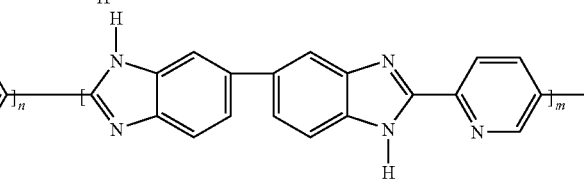

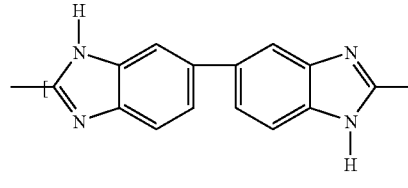
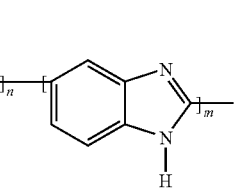

where n and m are each an integer greater than or equal to 10, preferably greater than or equal to 100.

The polyazoles obtainable by means of the described process, but in particular the polybenzimidazoles are characterized by a high molecular weight. Measured as the intrinsic viscosity, this is at least 1.4 dl/g and thus significantly higher than that of customary polybenzimidazole (IV<1.1 dl/g).

If the mixture in accordance with step A) also contains tricarboxylic acids or tetracarboxylic acid, branching/cross-linking of the formed polymer is achieved therewith. This contributes to an improvement in the mechanical property. The treatment of the polymer layer produced in accordance with step D) in the presence of moisture at temperatures and for a period of time until the layer exhibits a sufficient strength for use in fuel cells. The treatment can be effected to the extent that the membrane is self-supporting so that it can be detached from the support without any damage.

Furthermore, it has been found that when using aromatic dicarboxylic acids (or heteroaromatic dicarboxylic acid), such as isophthalic acid, terephthalic acid, 2,5-dihydroxyterephthalic acid, 4,6-dihydroxyisophthalic acid, 2,6-dihydroxyisophthalic acid, diphenic acid, 1,8-dihydroxynaphthalene-3,6-dicarboxylic acid, Diphenylether-4,4-dicarboxylic acid, benzophenone-4,4'-dicarboxylic acid, diphenylsulphone-4,4'-dicarboxylic acid, biphenyl-4,4'-dicarboxylic acid, 4-trifluoromethylphthalic acid, pyridine-2,5-dicarboxylic acid, pyridine-3,5-dicarboxylic acid, pyridine-2,6-dicarboxylic acid, pyridine-2,4-dicarboxylic acid, 4-phenyl-2,5-pyridinedicarboxylic acid, 3,5-pyrazoledicarboxylic acid, 2,6-pyrimidinedicarboxylic acid or 2,5-pyrazinedicarboxylic acid,
the temperature in step D)—or if the formation of oligomers and/or low-molecular weight polymers is already desired in step A)—in the range of up to 300° C., preferably between 100° C. and 250° C. is beneficial.

The treatment of the membrane in step E) is performed at temperatures of more than 0° C. and less than 150° C., preferably at temperatures between 10° C. and 120° C., in particular between room temperature (20° C.) and 90° C., in the presence of moisture or water and/or steam and/or water-containing phosphoric acid of up to 85% and/or in a mixture of a mixture containing organic phosphonic acids and/or sulphonic acids in water or phosphoric acid. The treatment is preferably performed at normal pressure, but can also be carried out with action of pressure. It is essential that the treatment takes place in the presence of sufficient moisture whereby the organic phosphonic anhydrides present contribute to the solidification of the membrane by means of partial hydrolysis with formation of organophosphonic acids and/or phosphoric acid (if polyphosphoric acid was also used).

The organophosphonic acids formed in the hydrolysis of the organic phosphonic anhydrides

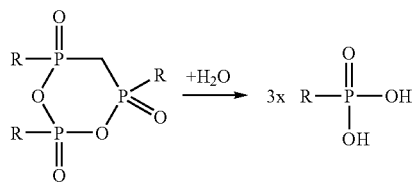

result in an unexpected reduction in the overvoltage, in particular at the cathode in the membrane electrode unit which is produced from the membrane according to the invention.

The partial hydrolysis of the organic phosphonic anhydrides in step E) leads to a solidification of the membrane and a reduction in the layer thickness and the formation of a membrane having a thickness between 15 and 3000 µm, preferably between 20 and 2000 µm, in particular between 20 and 1500 µm, which is self-supporting.

The upper temperature limit for the treatment in accordance with step E) is typically 150° C. With extremely short action of moisture, for example from overheated steam, this steam can also be hotter than 150° C. The duration of the treatment is substantial for the upper limit of the temperature.

The partial hydrolysis (step E) can also take place in climatic chambers where the hydrolysis can be specifically controlled with defined moisture action. In this connection, the moisture can be specifically set via the temperature or saturation of the surrounding area in contact with it, for example gases such as air, nitrogen, carbon dioxide or other suitable gases, or steam. The duration of the treatment depends on the parameters chosen as aforesaid.

Furthermore, the duration of the treatment depends on the thickness of the membrane.

Typically, the duration of the treatment amounts to a few seconds to minutes, for example with action of overheated steam, or up to whole days, for example in the open air at room temperature and lower relative humidity. Preferably, the duration of the treatment is 10 seconds to 300 hours, in particular 1 minute to 200 hours.

If the partial hydrolysis is performed at room temperature (20° C.) with ambient air having a relative humidity of 40-80%, the duration of the treatment is 1 to 200 hours.

The membrane obtained in accordance with step E) can be formed in such a way that it is self-supporting, i.e. it can be detached from the support without any damage and then directly processed further, if applicable.

The concentration of phosphonic acid and therefore the conductivity of the polymer membrane according to the invention can be set via the degree of hydrolysis, i.e. the duration, temperature and ambient humidity. According to the invention, the concentration of protons is given as the ion exchange capacity (IEC). Within the scope of the present invention, an IEC is at least 2 eq/g, preferably 5 eq/g, particularly preferably 10 eq/g.

Following the treatment in accordance with step E), the membrane can further be cross-linked at the surface by action of heat in the presence of atmospheric oxygen. This curing of the membrane surface additionally improves the properties of the membrane.

The cross-linking can also take place by action of IR or NIR (IR=infrared, i.e. light having a wavelength of more than 700 nm; NIR=near-IR, i.e. light having a wavelength in the range of from about 700 to 2000 nm and an energy in the range of from about 0.6 to 1.75 eV, respectively). Another method is β-ray irradiation. In this connection, the irradiation dose is from 5 and 200 kGy.

The polymer membrane according to the invention has improved material properties compared to the doped polymer membranes previously known. In particular, they exhibit better performances in comparison with known doped polymer membranes. The reason for this is in particular an improved proton conductivity. This is at least 0.1 S/cm, preferably at least 0.11 S/cm, in particular at least 0.12 S/cm at temperatures of 120° C.

In addition to the polymers based on polyazoles, the membranes according to the invention can also include further polymers as blend material. In this case, the function of the blend component is essentially to improve the mechanical properties and reduce the cost of material.

To this end, the additional blend material can be added during or after step A), step B) or step C). As the blend material, polyethersulphones, in particular the polyethersulphones described in the German patent application No. 10052242.4, come into consideration. The further polymers which can be employed as the blend component include, amongst others, polyolefines, such as poly(chloroprene), polyacetylene, polyphenylene, poly(p-xylylene), polyarylmethylene, polyarmethylene, polystyrene, polymethylstyrene, polyvinyl alcohol, polyvinyl acetate, polyvinyl ether, polyvinyl amine, poly(N-vinyl acetamide), polyvinyl imidazole, polyvinyl carbazole, polyvinyl pyrrolidone, polyvinyl pyridine, polyvinyl chloride, polyvinylidene chloride, polytetrafluoroethylene, polyhexafluoropropylene, copolymers of PTFE with hexafluoropropylene, with perfluoropropylvinyl ether, with trifluoronitrosomethane, with sulphonyl fluoride vinyl ether, with carbalkoxyperfluoroalkoxyvinyl ether, polychlorotrifluoroethylene, polyvinyl fluoride, polyvinylidene fluoride, polyacrolein, polyacrylamide, polyacrylonitrile, polycyanoacrylates, polymethacrylimide, cycloolefinic copolymers, in particular of norbornenes;

polymers having C—O bonds in the backbone, for example polyacetal, polyoxymethylene, polyether, polypropylene oxide, polyepichlorohydrin, polytetrahydrofuran, polyphenylene oxide, polyether ketone, polyester, in particular polyhydroxyacetic acid, polyethyleneterephthalate, polybutyleneterephthalate, polyhydroxybenzoate, polyhydroxypropionic acid, polypivalolacton, polycaprolacton, polymalonic acid, polycarbonate;

polymeric C—S bonds in the backbone, for example polysulphide ether, polyphenylenesulphide, polyethersulphone;

polymeric C—N bonds in the backbone, for example polyimines, polyisocyanides, polyetherimine, polyaniline, polyamides, polyhydrazides, polyurethanes, polyimides, polyazoles, polyazines;

liquid crystalline polymers, in particular Vetra, as well as inorganic polymers, such as polysilanes, polycarbosilanes, polysiloxanes, polysilicic acid, polysilicates, silicons, polyphosphazenes and polythiazyl.

For the application in fuel cells with a long-term service temperature above 100° C., such blend polymers that have a glass transition temperature or Vicat softening point VST/A/50 of at least 100° C., preferably at least 150° C. and especially particularly preferably at least 180° C., are preferred. In this connection, polysulphones with a Vicat softening point VST/A/50 of from 180° C. to 230° C. are preferred.

The preferred polymers include polysulphones, in particular polysulphone having aromatic groups in the backbone. According to a particular aspect of the present invention, preferred polysulphones and polyethersulphones have a melt volume rate MVR 300/21.6 of less than or equal to 40 cm$^3$/10 min, in particular less than or equal to 30 cm$^3$/10 min and particularly preferably less than or equal to 20 cm$^3$/10 min, measured in accordance with ISO 1133.

According to a particular aspect, the polymer membrane can comprise at least one polymer with aromatic sulphonic acid groups and/or phosphonic acid groups. Aromatic sulphonic acid groups and/or phosphonic acid groups are groups in which the sulphonic acid groups (—SO$_3$H) and/or phosphonic acid groups (—PO$_3$H$_2$) are bound covalently to an aromatic or heteroaromatic group. The aromatic group can be part of the backbone of the polymer or part of a side group where polymers having aromatic groups in the backbone are preferred. The sulphonic acid groups and/or phosphonic acid groups can in many cases also be employed in the form of their salts. Furthermore, derivatives, for example esters, in particular methyl or ethyl esters, or halides of the sulphonic acids can be used which are converted to the sulphonic acid during operation of the membrane.

Preferred aromatic or heteroaromatic groups are derived from benzene, naphthalene, biphenyl, diphenyl ether, diphenylmethane, diphenyldimethylmethane, bisphenone, diphenylsulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzooxadiazole, benzopyridine, benzopyrazine, benzopyrazidine, benzopyrimidine, benzotriazine, indolizine, pyridopyridine, imidazopyrimidine, pyrazinopyrimidine, carbazole, aziridine, phenazine, benzoquinoline, phenoxazine, phenothiazine, acridizine, benzopteridine, phenanthroline and phenanthrene which optionally also can be substituted. Preferred substituents are halogen atoms, e.g. fluorine, amino groups, hydroxy groups or alkyl groups.

In this case, the substitution pattern can be in any form, in the case of phenylene, for example, it can be ortho-, meta- and para-phenylene. Particularly preferred groups are derived from benzene and biphenylene which optionally also can be substituted.

Preferred alkyl groups are short-chain alkyl groups having 1 to 4 carbon atoms, e.g. methyl, ethyl, n- or i-propyl and t-butyl groups.

Preferred aromatic groups are phenyl or naphthyl groups. The alkyl groups and the aromatic groups can be substituted.

The polymers modified with sulphonic acid groups preferably have a content of sulphonic acid groups in the range of from 0.5 to 3 meq/g, preferably 0.5 to 2 meq/g. This value is determined through the so-called ion exchange capacity (IEC).

To measure the IEC, the sulphonic acid groups are converted to the free acid. To this end, the polymer is treated in a known way with acid, removing excess acid by washing. Thus, the sulphonated polymer is initially treated for 2 hours in boiling water. Subsequently, excess water is dabbed off and the sample is dried at 160° C. in a vacuum drying cabinet at p<1 mbar for 15 hours. Then, the dry weight of the membrane is determined. The polymer thus dried is then dissolved in DMSO at 80° C. for 1 h. Subsequently, the solution is titrated with 0.1M NaOH. The ion exchange capacity (IEC) is then calculated from the consumption of acid to reach the equivalence point and from the dry weight.

Polymers with sulphonic acid groups covalently bound to aromatic groups are known in professional circles. Polymers with aromatic sulphonic acid groups can, for example, be produced by sulphonation of polymers. Processes for the sulphonation of polymers are described in F. Kucera et al., Polymer Engineering and Science 1988, Vol. 38, No. 5, 783-792. In this connection, the sulphonation conditions can be chosen such that a low degree of sulphonation develops (DE-A-19959289).

With regard to polymers having aromatic sulphonic acid groups whose aromatic radicals are part of the side group, particular reference shall be made to polystyrene derivatives. The document U.S. Pat. No. 6,110,616 for instance describes copolymers of butadiene and styrene and their subsequent sulphonation for use in fuel cells.

Furthermore, such polymers can also be obtained by polyreactions of monomers which comprise acid groups. Thus, perfluorinated polymers as described in U.S. Pat. No. 5,422,411 can be produced by copolymerisation of trifluorostyrene and sulphonyl-modified trifluorostyrene.

According to a particular aspect of the present invention, thermoplastics stable at high temperatures which include sulphonic acid groups bound to aromatic groups are employed. In general, such polymers have aromatic groups in the backbone. Thus, sulphonated polyether ketones (DE-A-4219077, WO96/01177), sulphonated polysulphones (J. Membr. Sci.

83 (1993), p. 211) or sulphonated polyphenylenesulphide (DE-A-19527435) are preferred.

The polymers set forth above which have sulphonic acid groups bound to aromatic groups can be used individually or as a mixture where mixtures having polymers with aromatic groups in the backbone are particularly preferred.

The molecular weight of the polymers having sulphonic acid groups bound to aromatic groups can vary widely, depending on the type of polymer and its processability. Preferably, the weight average of the molecular weight $M_w$ is in the range of from 5000 to 10,000,000, in particular 10,000 to 1,000,000, particularly preferably 15,000 to 50,000. According to a particular aspect of the present invention, polymers with sulphonic acid groups bound to aromatic groups which have a low polydispersity index $M_w/M_n$ are. Preferably, the polydispersity index is in the range of from 1 to 5, in particular 1 to 4.

To improve the properties in terms of application technology further, fillers, in particular proton-conducting fillers, and additional acids can additionally be added to the membrane. The addition can be performed either during or after step A), step B) or step C).

Non-limiting examples of proton-conducting fillers are sulphates, such as
$CsHSO_4$, $Fe(SO_4)_2$, $(NH_4)_3H(SO_4)_2$, $LiHSO_4$, $NaHSO_4$, $KHSO_4$, $RbSO_4$, $LiN_2H_5SO_4$, $NH_4HSO_4$,
phosphates, such as
$Zr_3(PO_4)_4$, $Zr(HPO_4)_2$, $HZr_2(PO_4)_3$, $UO_2PO_4 \cdot 3H_2O$, $H_8UO_2PO_4$, $Ce(HPO_4)_2$, $Ti(HPO_4)_2$, $KH_2PO_4$, $NaH_2PO_4$, $LiH_2PO_4$, $NH_4H_2PO_4$, $CsH_2PO_4$, $CaHPO_4$, $MgHPO_4$, $HSbP_2O_8$, $HSb_3P_2O_{14}$, $H_5Sb_5P_2O_{20}$,
polyacid, such as
$H_3PW_{12}O_{40} \cdot nH_2O$ (n=21-29), $H_3SiW_{12}O_{40} \cdot nH_2O$ (n=21-29), $H_xWO_3$, $HSbWO_6$, $H_3PMo_{12}O_{40}$, $H_2Sb_4O_{11}$, $HTaWO_6$, $HNbO_3$, $HTiNbO_5$, $HTiTaO_5$, $HSbTeO_6$, $H_5Ti_4O_9$, $HSbO_3$, $H_2MoO_4$
selenides and arsenides, such as
$(NH_4)_3H(SeO_4)_2$, $UO_2AsO_4$, $(NH_4)_3H(SeO_4)_2$, $KH_2AsO_4$, $Cs_3H(SeO_4)_2$, $Rb_3H(SeO_4)_2$,
phosphides, such as ZrP, TiP, HfP
oxides, such as $Al_2O_3$, $Sb_2O_5$, $ThO_2$, $SnO_2$, $ZrO_2$, $MoO_3$
silicates, such as zeolites, zeolites($NH_4$+), phyllosilicates, tectosilicates, H-natrolites, H-mordenites, $NH_4$-analcines, $NH_4$-sodalites, $NH_4$-gallates, H-montmorillonites
acids, such as $HClO_4$, $SbF_5$
fillers, such as carbides, in particular SiC, $Si_3N_4$, fibres, in particular glass fibres, glass powders and/or polymer fibres, preferably based on polyazoles.

As a further component, this membrane can also contain perfluorinated sulphonic acid additives (0.1-20 wt-%, preferably 0.2-15 wt-%, especially preferably 0.2-10 wt-%). These additives result in an improvement in performance, to an increase in oxygen solubility and oxygen diffusion in the vicinity of the cathode and to a reduction in adsorption of phosphoric acid and phosphate onto platinum. (Electrolyte additives for phosphoric acid fuel cells. Gang, Xiao; Hjuler, H. A.; Olsen, C.; Berg, R. W.; Bjerrum, N. J. Chem. Dep. A, Tech. Univ. Denmark, Lyngby, Den. J. Electrochem. Soc. (1993), 140(4), 896-902, and Perfluorosulfonimide as an additive in phosphoric acid fuel cell. Razaq, M.; Razaq, A.; Yeager, E.; DesMarteau, Darryl D.; Singh, S. Case Cent. Electrochem. Sci., Case West, Reserve Univ., Cleveland, Ohio, USA. J. Electrochem. Soc. (1989), 136(2), 385-90.)

Non-limiting examples of persulphonated additives are: trifluoromethanesulphonic acid, potassium trifluoromethanesulphonate, sodium trifluoromethanesulphonate, lithium trifluoromethanesulphonate, ammonium trifluoromethanesulphonate, potassium perfluorohexanesulphonate, sodium perfluorohexanesulphonate, lithium perfluorohexanesulphonate, ammonium perfluorohexanesulphonate, perfluorohexanesulphonic acid, potassium nonafluorobutanesulphonate, sodium nonafluorobutanesulphonate, lithium nonafluorobutanesulphonate, ammonium nonafluorobutanesulphonate, cesium nonafluorobutanesulphonate, triethylammonium perfluorohexasulphonate, perfluorosulphonimides and Nafion.

As a further component, the membrane can also contain additives which scavenge (primary antioxidants) or destroy (secondary antioxidants) the free peroxide radicals produced in the oxygen reduction during operation and thereby improve the life and stability of the membrane and membrane electrode unit as described in JP2001118591 A2. The functionality and molecular structures of such additives are described in F. Gugumus in Plastics Additives, Hanser Veriag, 1990; N. S. Allen, M. Edge Fundamentals of Polymer Degradation and Stability, Elsevier, 1992; or H. Zweifel, Stabilization of Polymeric Materials, Springer, 1998.

Non-limiting examples of such additives are:
bis(trifluoromethyl) nitroxide, 2,2-diphenyl-1-picrinylhydrazyl, phenols, alkylphenols, sterically hindered alkylphenols, such as for example Irganox, aromatic amines, sterically hindered amines, such as for example Chimassorb; sterically hindered hydroxylamines, sterically hindered alkylamines, sterically hindered hydroxylamines, sterically hindered hydroxylamine ethers, phosphites, such as for example Irgafos, nitrosobenzene, methyl-2-nitrosopropane, benzophenone, benzaldehyde tert-butyl nitrone, cysteamine, melanines, lead oxides, manganese oxides, nickel oxides, cobalt oxides.

Possible fields of use for the doped polymer membranes according to the invention include, amongst others, the use in fuel cells, electrolysis, capacitors and battery systems. Owing to their property profile, the doped polymer membranes are preferably used in fuel cells.

The present invention also relates to a membrane electrode unit which includes at least one polymer membrane according to the invention. For further information on membrane electrode units, reference is made to the technical literature, in particular the U.S. Pat. No. 4,191,618, U.S. Pat. No. 4,212, 714 and U.S. Pat. No. 4,333,805. The disclosure contained in the above-mentioned citations [U.S. Pat. No. 4,191,618, U.S. Pat. No. 4,212,714 und U.S. Pat. No. 4,333,805] with respect to the structure and production of membrane electrode units as well as the electrodes, gas diffusion layers and catalysts to be chosen is also part of the description.

In a variant of the present invention, the membrane formation can also be performed directly on the electrode rather than on a support. Through this, the treatment in accordance with step E) can be correspondingly shortened since it is no longer required for the membrane to be self-supporting. Such a membrane is also an object of the present invention.

A further object of the present invention is an electrode having a proton-conducting polymer coating based on polyazoles which can be obtained by a process comprising the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C., preferably up to 300° C., B) dissolving the solid prepolymer obtained in accordance with step A) in organic phosphonic anhydrides with formation of a solution and/or dispersion, C) heating the solution obtainable in accordance with step B) under inert gas to temperatures of up to 300° C. preferably up to 280° C., with formation of the dissolved polyazole polymer, D) applying a layer using the mixture in accordance with step C) to an electrode, E) treatment of the layer formed in step D).

The variants described above and the preferred embodiments also apply to this object so that they will not be repeated at this point.

The coating has, following step E), a thickness between 2 and 3000 μm, preferably between 3 and 2000 μm, in particular between 5 and 1500 μm.

An electrode coated in such a way can be integrated into a membrane electrode unit which optionally includes at least one polymer membrane according to the invention.

General Measurement Methods:

Measurement Method for IEC

The conductivity of the membranes depends strongly on the content of acid groups, expressed as the so-called ion exchange capacity (IEC). To measure the ion exchange capacity, a specimen having a diameter of 3 cm is punched out and placed in a beaker filled with 100 ml of water. The acid released is titrated with 0.1M NaOH. Subsequently, the specimen is removed, excess water is dabbed off and the sample is dried at 160° C. over 4 h. The dry weight, $m_0$, is then determined gravimetrically with an accuracy of 0.1 mg. Thereafter, the ion exchange capacity is calculated from the consumption of the 0.1 μm NaOH until reaching the first titration endpoint, $V_1$ in ml, and from the dry weight, $m_0$ in mg, according to the following formula:

$$IEC = V_1 * 300/m_0$$

Measurement Method for Specific Conductivity

The specific conductivity is measured by means of impedancy spectroscopy in a 4-pole arrangement in potentiostatic mode and using platinum electrodes (wire, diameter of 0.25 mm). The distance between the current-collecting electrodes is 2 cm. The spectrum obtained is evaluated using a simple model comprised of a parallel arrangement of an ohmic resistance and a capacitor. The cross-section of the specimen of the membrane doped with phosphoric acid is measured immediately before mounting the specimen. To measure the temperature dependency, the measurement cell is brought to the desired temperature in an oven and regulated using a Pt-100 thermocouple arranged in the immediate vicinity of the specimen. After the temperature has been reached, the specimen is kept at this temperature for 10 minutes before beginning the measurement.

The invention claimed is:

1. A proton-conducting polymer membrane based on polyazoles which is obtained by a process comprising the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C., B) dissolving the solid prepolymer obtained in accordance with step A) in an organic phosphonic anhydride with formation of a solution and/or dispersion, and said organic phosphonic anhydride is of the formula

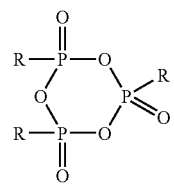

or a linear compound of the formula

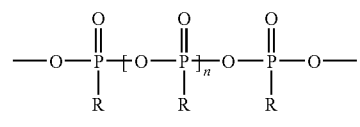

n ≥ 0 or an anhydride of the multiple organic phosphonic acids of the formula

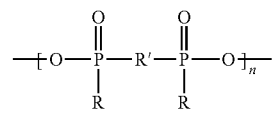

n ≥ 1 wherein the radicals R and R' are identical or different and represent $C_1$-$C_{20}$-alkyl, $C_1$-$C_{20}$ fluoroalkyl, $C_6$-$C_{20}$ aryl, $C_6$-$C_{20}$ fluoroaryl, $C_1$-$C_{20}$ alkoxy, $C_6$-$C_{20}$ aryloxy, $C_7$-$C_{20}$ arylalkyl, $C_7$-$C_{20}$ alkylaryl, $C_7$-$C_{20}$ aryloxyalkyl, $C_{12}$-$C_{20}$ aryloxyaryl, $C_5$-$C_{20}$ heteroaryl, $C_4$-$C_{20}$ heterocycloalkyl, heteroatom-containing group, where one or more $C_1$-$C_{20}$ carbon-containing groups can form a cyclic system, C) heating the solution obtainable in accordance with step B) under inert gas to temperatures of up to 300° C. with formation of the dissolved polyazole polymer, D) forming a membrane using the solution of the polyazole polymer in accordance with step C) on a support and E) treating the membrane formed in step D) in the presence of moisture at temperatures and for a period of time until the membrane is self-supporting and can be detached from the support without any damage.

2. The membrane as claimed in claim 1 wherein the process comprises the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 300° C., B) dissolving the solid prepolymer obtained in accordance with step A) in an organic phosphonic anhydrides with formation of a solution and/or dispersion, C) heating the solution obtainable in accordance with step B) under inert gas to temperatures of up to 280° C., with formation of the dissolved polyazole polymer, D) forming a membrane using the solution of the polyazole polymer in accordance with step C) on a support and E) treating the membrane formed in step D) in the presence of moisture at temperatures and for a period of time until the membrane is self-supporting and can be detached from the support without any damage.

3. The membrane according to claim 1, wherein said aromatic tetramino compounds are 3,3',4,4'-tetraminobiphenyl, 2,3,5,6-tetraminopyridine, 1,2,4,5-tetraminobenzene, 3,3',4,4'-tetraminodiphenyl sulphone, 3,3',4,4'-tetraminodiphenyl ether, 3,3',4,4'-tetraminobenzophenone, 3,3',4,4'-tetraminodiphenylmethane or 3,3',4,4'-tetraminodiphenyldimethylmethane.

4. The membrane according to claim 1, wherein said aromatic dicarboxylic acids are isophthalic acid, terephthalic acid, phthalic acid, 5-hydroxyisophthalic acid, 4-hydroxyisophthalic acid, 2-hydroxyterephthalic acid, 5-aminoisophthalic acid, 5-N,N-dimethylaminoisophthalic acid, 5-N,N-diethylaminoisophthalic acid, 2,5-dihydroxyterephthalic acid, 2,5-dihydroxyisophthalic acid, 2,3-dihydroxyphthalic acid, 2,4-dihydroxyphthalic acid, 3,4-dihydroxyphthalic acid, 3-fluorophthalic acid, 5-fluoroisophthalic acid, 2-fluoroterephthalic acid, tetrafluorophthalic acid, tetrafluoroisophthalic acid, tetrafluoroterephthalic acid, 1,4-naphthalenedicarboxylic acid, 1,5-naphthalenedicarboxylic acid, 2,6-naphthalenedicarboxylic acid, 2,7-naphthalenedicarboxylic acid, diphenic acid, 1,8-dihydroxynaphthalene-3,6-dicarboxylic acid, diphenyl ether-4,4'-dicarboxylic acid, benzophenone-4,4'-dicarboxylic acid, diphenylsulphone-4,4'-dicarboxylic acid, biphenyl-4,4'-dicarboxylic acid, 4-trifluoromethylphthalic acid, 2,2-bis(4-carboxyphenyl)hexafluoropropane, 4,4'-stilbenedicarboxylic acid, 4-carboxycinnamic acid or their C1-C20 alkyl esters or C5-C12 aryl esters or their acid anhydrides or their acid chlorides.

5. The membrane according to claim 1, wherein said aromatic carboxylic acids are tricarboxylic acids, tetracarboxylic acids or their C1-C20 alkyl esters or C5-C12 aryl esters or their acid anhydrides or their acid chlorides.

6. The membrane according to claim 2, wherein said aromatic carboxylic acids are 1,3,5-benzenetricarboxylic acid (trimesic acid), 1,2,4-benzenetricarboxylic acid (trimellitic acid); (2-carboxyphenyl)iminodiacetic acid, 3,5,3'-biphenyltricarboxylic acid, 3,5,4'-biphenyltricarboxylic acid and/or 2,4,6-pyridinetricarboxylic acid.

7. The membrane according to claim 2, wherein said aromatic carboxylic acids are benzene-1,2,4,5-tetracarboxylic acid; naphthalene-1,4,5,8-tetracarboxylic acid; 3,5,3',5'-biphenyltetracarboxylic acid; benzophenonetetracarboxylic acid, 3,3',4,4'-biphenyltetracarboxylic acid, 2,2',3,3'-biphenyltetracarboxylic acid, 1,2,5,6-naphthalenetetracarboxylic acid, or 1,4,5,8-naphthalenetetracarboxylic acid.

8. The membrane according to claim 5, wherein the content of tricarboxylic acid or tetracarboxylic acids (based on dicarboxylic acid used) is between 0 and 30 mol %.

9. The membrane according to claim 5, wherein the content of tricarboxylic acid or tetracarboxylic acids (based on dicarboxylic acid used) is between 0.5 and 10 mol-%.

10. The membrane according to claim 1, wherein said heteroaromatic carboxylic acids are heteroaromatic dicarboxylic acids, tricarboxylic acids or tetracarboxylic acids, which contain at least one nitrogen, oxygen, sulphur or phosphorus atom in the aromatic group.

11. The membrane according to claim 2, wherein said heteroaromatic carboxylic acids are pyridine-2,5-dicarboxylic acid, pyridine-3,5-dicarboxylic acid, pyridine-2,6-dicarboxylic acid, pyridine-2,4-dicarboxylic acid, 4-phenyl-2,5-pyridinedicarboxylic acid, 3,5-pyrazoledicarboxylic acid, 2,6-pyrimidinedicarboxylic acid, 2,5-pyrazinedicarboxylic acid, 2,4,6-pyridinetricarboxylic acid, benzimidazole-5,6-dicarboxylic acid as well as their C1-C20 alkyl esters or C5-C12 aryl esters or their acid anhydrides or their acid chlorides.

12. The membrane according to claim 1, wherein, in step B), further comprises a polyphosphoric acid having a content of at least 83%, calculated as $P_2O_5$ (by acidimetry).

13. The membrane according to claim 1, wherein, in step B) further comprises $P_2O_5$.

14. The membrane according to claim 1, wherein, in step B) or step C), a solution or a dispersion/suspension is produced.

15. The membrane according to claim 1, wherein, in step C), a polymer based on polyazole containing recurring azole units of the formula (I) and/or (II) and/or (III) and/or (IV) and/or (V) and/or (VI) and/or (VII) and/or (VIII) and/or (IX) and/or (X) and/or (XI) and/or (XII) and/or (XIII) and/or (XIV) and/or (XV) and/or (XVI) and/or (XVI) and/or (XVII) and/or (XVIII) and/or (XIX) and/or (XX) and/or (XXI) and/or (XXII) is formed

(I)

(II)

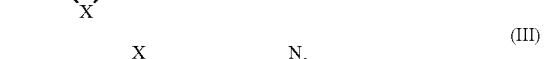

(III)

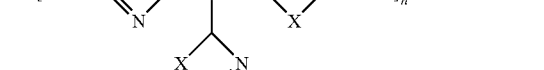

(IV)

(V)

(VI)

(VII)

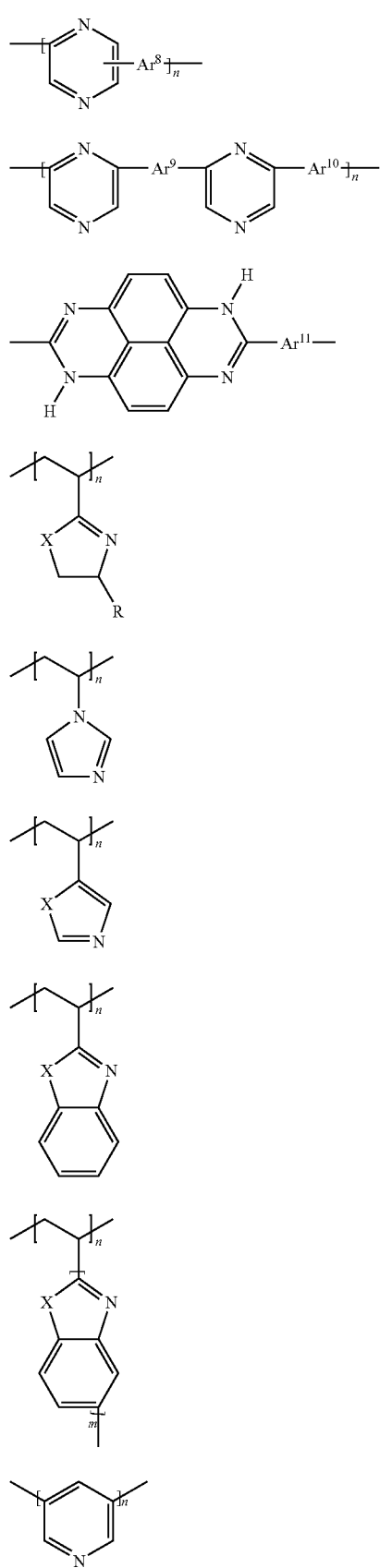
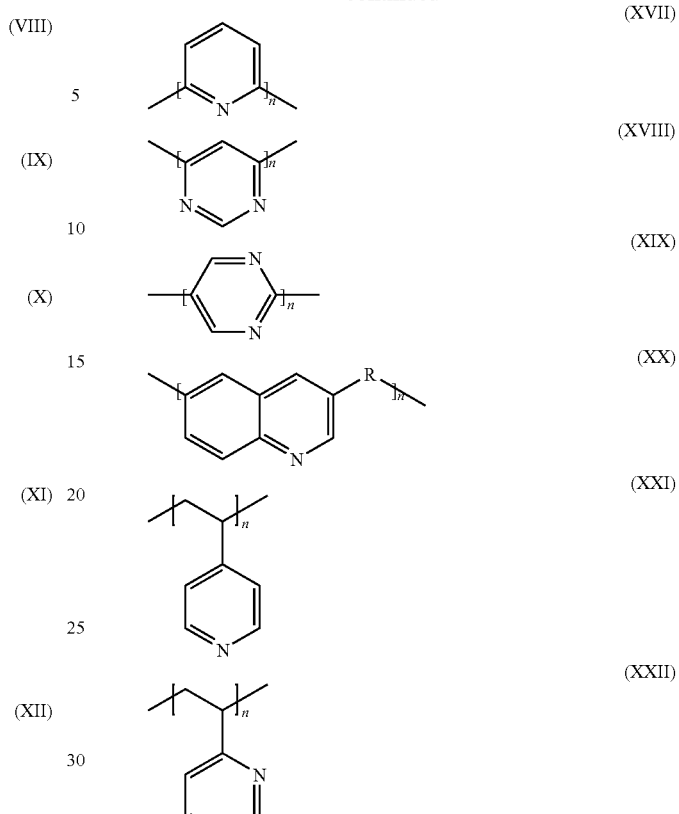

wherein
Ar are identical or different and represent a tetracovalent aromatic or heteroaromatic group which can be mononuclear or polynuclear,
Ar¹ are identical or different and represent a bicovalent aromatic or heteroaromatic group which can be mononuclear or polynuclear,
Ar² are identical or different and represent a bicovalent or tricovalent aromatic or heteroaromatic group which can be mononuclear or polynuclear,
Ar³ are identical or different and represent a tricovalent aromatic or heteroaromatic group which can be mononuclear or polynuclear,
Ar⁴ are identical or different and represent a tricovalent aromatic or heteroaromatic group which can be mononuclear or polynuclear,
Ar⁵ are identical or different and represent a tetracovalent aromatic or heteroaromatic group which can be mononuclear or polynuclear,
Ar⁶ are identical or different and represent a bicovalent aromatic or heteroaromatic group which can be mononuclear or polynuclear,
Ar⁷ are identical or different and represent a bicovalent aromatic or heteroaromatic group which can be mononuclear or polynuclear,
Ar⁸ are identical or different and represent a tricovalent aromatic or heteroaromatic group which can be mononuclear or polynuclear,
Ar⁹ are identical or different and represent a bicovalent or tricovalent or tetracovalent aromatic or heteroaromatic group which can be mononuclear or polynuclear,
Ar¹⁰ are identical or different and represent a bicovalent or tricovalent aromatic or heteroaromatic group which can be mononuclear or polynuclear, Ar¹¹ are identical or different and represent a bicovalent aromatic or heteroaromatic group which can be mononuclear or polynuclear, X are identical or different and represent oxygen, sulphur or an amino group which carries a hydrogen atom, a group having 1-20 carbon atoms, preferably a branched or unbranched alkyl or alkoxy group, or an aryl group as a further radical, R are identical or different and represent hydrogen, an alkyl group and an aromatic group, with the proviso that R in formula (XX) is not hydrogen, and n and m are identical or different and each are an integer greater than or equal to 10.

16. The membrane according to claim 1, wherein, in step C), a polymer selected from the group consisting of polybenzimidazole, poly(pyridines), poly(pyrimidines), polyimidazoles, polybenzothiazoles, polybenzoxazoles, polyoxadiazoles, polyquinoxalines, polythiadiazoles and poly(tetrazapyrenes) is formed.

17. The membrane according to claim 1, wherein, in step C), a polymer containing recurring benzimidazole units of the formula

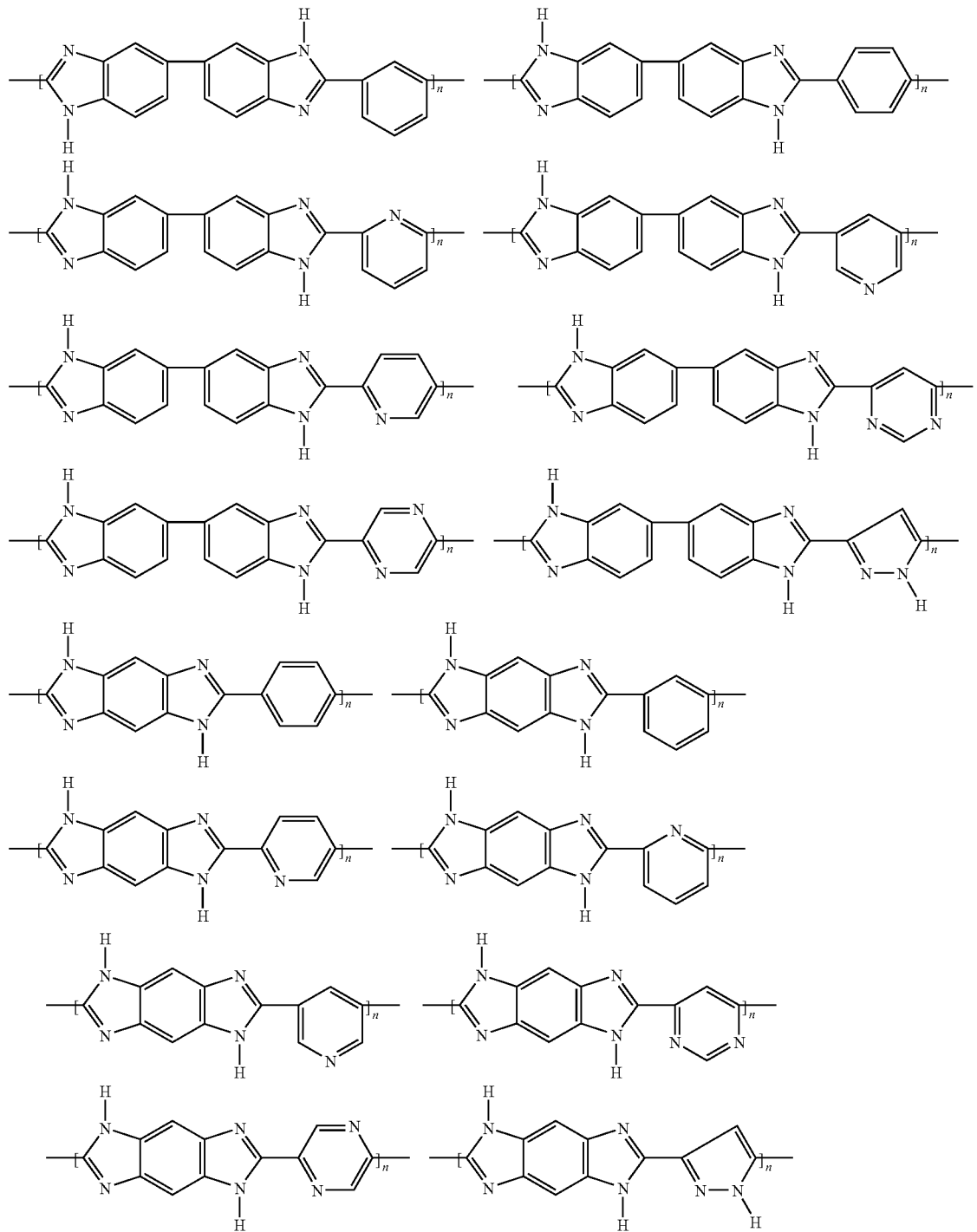

-continued

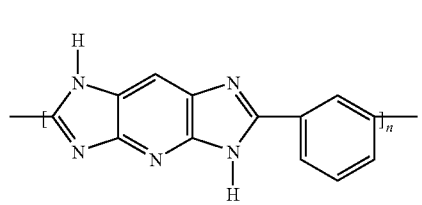
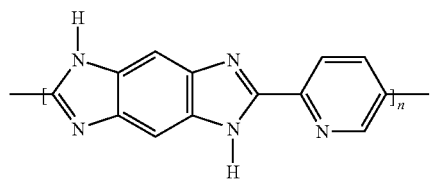
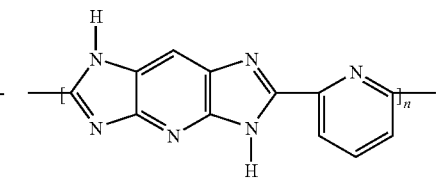
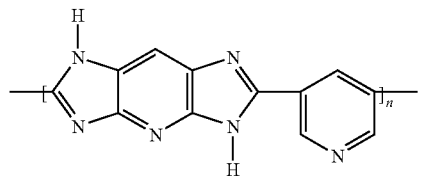
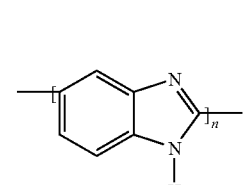
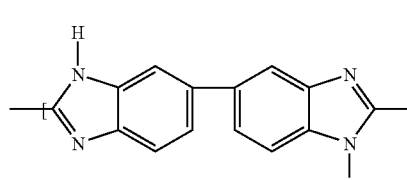
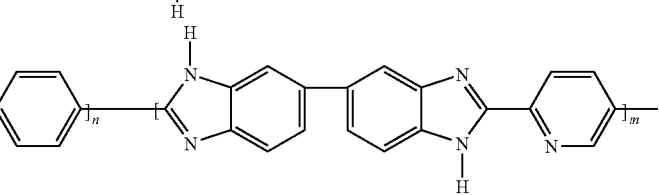
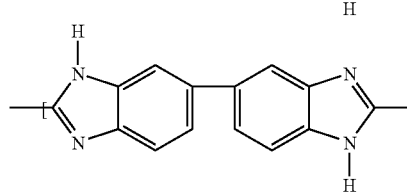

where n and m are each an integer greater than or equal to 10 is formed.

18. The membrane according to claim 1, wherein, during or after step A), step B), step C), a further polymer is added as blend material.

19. The membrane according to claim 1, wherein, after step C) and before step D), the viscosity is adjusted by addition of phosphoric acid and/or organophosphonic acids.

20. The membrane according to claim 1, wherein the treatment of the membrane in step E) is performed at temperatures of more than 0° C. and less than 150° C. in the presence of moisture or water and/or steam.

21. The membrane according to claim 1, wherein the treatment of the membrane in step E) is performed at temperatures of between room temperature (20° C.) and 90° C., in the presence of moisture or water and/or steam and for 1 minute to 200 hours.

22. The membrane according to claim 1, wherein the treatment of the membrane in step E) is for 10 seconds to 300 hours.

23. The membrane according to claim 1, wherein, in step D), an electrode is chosen as the support and the treatment in accordance with step E) is such that the membrane formed is no longer self-supporting.

24. The membrane according to claim 1, wherein, in step D), a layer having a thickness of 20 to 4000 μm is produced.

25. The membrane according to claim 1, wherein the membrane formed in step E) has a thickness between 15 and 3000 μm.

26. The membrane according to claim 1, wherein the membrane formed in step E) has a thickness between 20 and 1500 μm.

27. An electrode having a proton-conducting polymer coating based on polyazoles which can be obtained by a process comprising the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C., B) dissolving the solid prepolymer obtained in accordance with step A) in an organic phosphonic anhydride with formation of a solution and/or dispersion, and said organic phosphonic anhydride is of the formula

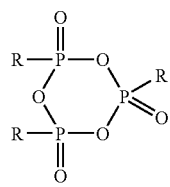

or a linear compound of the formula

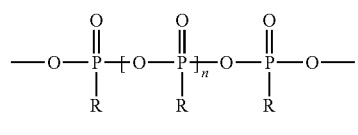

or an anhydride of the multiple organic phosphonic acids of the formula

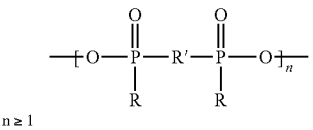

n ≥ 1 wherein the radicals R and R' are identical or different and represent $C_1$-$C_{20}$-alkyl, $C_1$-$C_{20}$ fluoroalkyl, $C_6$-$C_{20}$ aryl, $C_6$-$C_{20}$ fluoroaryl, $C_1$-$C_{20}$ alkoxy, $C_6$-$C_{20}$ aryloxy, $C_7$-$C_{20}$ arylalkyl, $C_7$-$C_{20}$ alkylaryl, $C_7$-$C_{20}$ aryloxyalkyl, $C_{12}$-$C_{20}$ aryloxyaryl, $C_5$-$C_{20}$ heteroaryl, $C_4$-$C_{20}$ heterocycloalkyl, $C_2$-$C_{20}$ heteroatom-containing group, where one or more $C_1$-$C_{20}$ carbon-containing groups can form a cyclic system, C) heating the solution obtainable in accordance with step B) under inert gas to temperatures of up to 300° C. with formation of the dissolved polyazole polymer,
 D) forming a layer using the solution of the polyazole polymer in accordance with step C) on an electrode and
 E) treating the layer formed in step D).

28. The electrode according to claim 27, wherein the coating has a thickness between 2 and 3000 μm.

29. The electrode according to claim 27, wherein the coating has a thickness between 5 and 1500 μm.

30. A membrane electrode unit containing at least one electrode and at least one membrane according to claim 1.

31. The membrane electrode unit containing at least one electrode according to claim 30 and at least one membrane based on polyazoles which is obtained by a process comprising the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C.,
 B) dissolving the solid prepolymer obtained in accordance with step A) in an organic phosphonic anhydride with formation of a solution and/or dispersion, and said organic phosphonic anhydride is of the formula

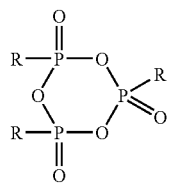

or a linear compound of the formula

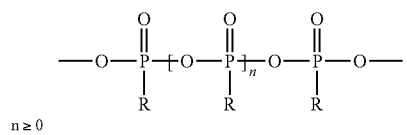

n ≥ 0 or an anhydride of the multiple organic phosphonic acids of the formula

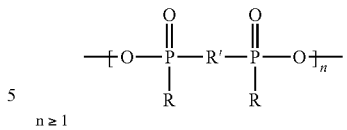

n ≥ 1 wherein the radicals R and R' are identical or different and represent $C_1$-$C_{20}$-alkyl, $C_1$-$C_{20}$ fluoroalkyl, $C_6$-$C_{20}$ aryl, $C_6$-$C_{20}$ fluoroaryl, $C_1$-$C_{20}$ alkoxy, $C_6$-$C_{20}$ aryloxy, $C_7$-$C_{20}$ arylalkyl, $C_7$-$C_{20}$ alkylaryl, $C_7$-$C_{20}$ aryloxyalkyl, $C_{12}$-$C_{20}$ aryloxyaryl, $C_5$-$C_{20}$ heteroaryl, $C_4$-$C_{20}$ heterocycloalkyl, $C_2$-$C_{20}$ heteroatom-containing group, where one or more $C_1$-$C_{20}$ carbon-containing groups can form a cyclic system, C) heating the solution obtainable in accordance with step B) under inert gas to temperatures of up to 300° C. with formation of the dissolved polyazole polymer,
 D) forming a membrane using the solution of the polyazole polymer in accordance with step C) on a support and
 E) treating the membrane formed in step D) until it is self-supporting.

32. A fuel cell containing one or more membrane electrode units according to claim 30.

33. A process to produce a proton-conducting polymer membrane which comprises the steps of A) reacting one or more aromatic tetramino compounds with one or more aromatic carboxylic acids or their esters which contain at least two acid groups per carboxylic acid monomer, or one or more aromatic and/or heteroaromatic diaminocarboxylic acids in the melt at temperatures of up to 350° C.,
 B) dissolving the solid prepolymer obtained in accordance with step A) in an organic phosphonic anhydride with formation of a solution and/or dispersion, and said organic phosphonic anhydride is of the formula

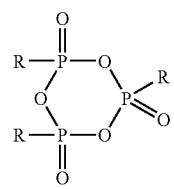

or a linear compound of the formula

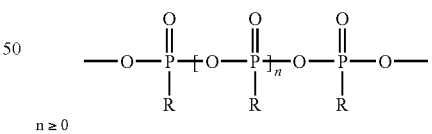

n ≥ 0 or an anhydride of the multiple organic phosphonic acids of the formula

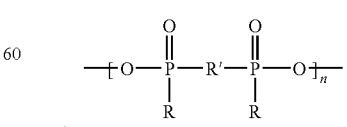

n ≥ 1 wherein the radicals R and R' are identical or different and represent $C_1$-$C_{20}$-alkyl, $C_1$-$C_{20}$ fluoroalkyl, $C_6$-$C_{20}$ aryl, $C_6$-$C_{20}$ fluoroaryl, $C_1$-$C_{20}$ alkoxy, $C_6$-$C_{20}$ aryloxy, $C_7$-$C_{20}$ arylalkyl, $C_7$-$C_{20}$ alkylaryl, $C_7$-$C_{20}$ aryloxyalkyl, $C_{12}$-$C_{20}$ aryloxyaryl, $C_5$-$C_{20}$ heteroaryl, $C_4$-$C_{20}$ heterocycloalkyl, $C_2$-$C_{20}$ heteroatom-containing group, where one or more $C_1$-$C_{20}$ carbon-containing groups can form a cyclic system,
   C) heating the solution obtainable in accordance with step B) under inert gas to temperatures of up to 300° C. with formation of the dissolved polyazole polymer,
   D) forming a membrane using the solution of the polyazole polymer in accordance with step C) on a support and
   E) treating the membrane formed in step D) until it is self-supporting.

34. The membrane according to claim 1, wherein, in step D), a layer having a thickness between 30 and 3500 μm is produced.

35. The electrode according to claim 1, wherein the radicals R and R' are identical or different and represent methyl, ethyl, n-propyl, i-propyl, n-butyl, i-butyl, s-butyl, t-butyl, n-pentyl, s-pentyl, cyclopentyl, n-hexyl, cyclohexyl, n-octyl, cyclooctyl, phenyl, biphenyl, naphthyl, anthracenyl, trifluoromethyl, pentafluoroethyl, 2,2,2-trifluoroethyl, triphenylenyl, [1,1;3',1"]-terphenyl-2'-yl, binaphthyl, phenanthrenyl, tetrafluorophenyl, heptafluoronaphthyl, methoxy, ethoxy, n-propoxy, i-propoxy, n-butoxy, i-butoxy, s-butoxy, t-butoxy, phenoxy, naphthoxy, biphenyloxy, anthracenyloxy, phenanthrenyloxy, phenoxy, naphthoxy, biphenyloxy, anthracenyloxy, phenanthrenyloxy, o-tolyl, m-tolyl, p-tolyl, 2,6-dimethylphenyl, 2,6-diethylphenyl, 2,6-di-1-propylphenyl, 2,6-di-t-butylphenyl, o-t-butylphenyl, m-t-butylphenyl, p-t-butylphenyl, benzyl, ethylphenyl, propylphenyl, diphenylmethyl, triphenylmethyl, naphthalenylmethyl, o-methoxyphenyl, m-phenoxymethyl, p-phenoxymethyl, p-phenoxyphenyl, 2-pyridyl, 3-pyridyl, 4-pyridyl, quinolinyl, isoquinolinyl, acridinyl, benzoquinolinyl, benzoisoquinolinyl, furyl, benzofuryl, 2-pyrrolidinyl, 2-indolyl, 3-indolyl, 2,3-dihydroindolyl, carbonyl, benzoyl, oxybenzoyl, benzoyloxy, acetyl, acetoxy or nitric.

* * * * *